United States Patent [19]

Aumüller et al.

[11] 3,939,269
[45] Feb. 17, 1976

[54] BENZENESULFONYL-SEMICARBAZIDES FOR LOWERING BLOOD SUGAR LEVELS

[75] Inventors: Walter Aumüller, Kelkheim, Taunus; Rudi Weyer, Frankfurt am Main; Ruth Heerdt, Mannheim, all of Germany

[73] Assignee: Hoechst Aktiengesellschaft, Frankfurt am Main, Germany

[22] Filed: Jan. 18, 1973

[21] Appl. No.: 324,836

Related U.S. Application Data

[62] Division of Ser. No. 149,746, June 3, 1971.

[30] Foreign Application Priority Data

Apr. 26, 1971 Germany............................ 2120266

[52] U.S. Cl. ................................................ 424/258
[51] Int. Cl............................................. A61k 27/00
[58] Field of Search...... 260/239 E, 239 BD, 287 R, 260/283 SA; 424/258

[56] References Cited
UNITED STATES PATENTS

| | | |
|---|---|---|
| 3,041,331 | 6/1962 | Wright........................ 260/553 D X |
| 3,239,503 | 3/1966 | Kovgeu et al............... 260/553 D X |
| 3,549,645 | 12/1970 | Heerdt et al.............. 260/553 DA X |
| 3,655,756 | 4/1972 | Weber et al.............. 260/553 DA X |

OTHER PUBLICATIONS

Ambrogi et al., Avzneim–Forsch 1971, Vol. 21, pp. 200–207. 207.
Kuvzcr, Chem. Reviews Vol. 50, p. 27, (1952).

*Primary Examiner*—Jerome D. Goldberg
*Attorney, Agent, or Firm*—Curtis, Morris & Safford

[57] ABSTRACT

Hypoglycemically active benzenesulfonyl-semicarbazides of the formula

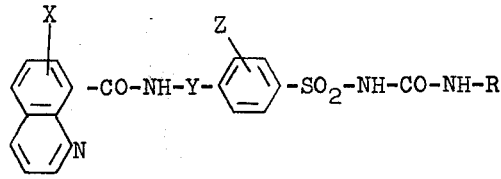

wherein X is hydrogen, chlorine, bromine, methyl or methoxy, Y is —CH(CH$_3$)-CH$_2$—, preferably —CH$_2$—CH$_2$—, Z is hydrogen or a hydrocarbon radical of 1 or 2 carbon atoms, which forms together with Y a 5- or 6-membered ring, R is alkylene-imino of 3 to 7 carbon atoms in the ring which may be unsaturated or substituted by 1 or 2 methyl or lower alkyl or methoxy, pentamethylene-imino substituted by endoalkylene of 1 to 3 carbon atoms, hexamethylene-imino substituted by endoethylene in β- ε-position, tetrahydro-iso-indoline, 4,7-endoalkylenehexahydro- or -tetrahydro-iso-indoline, the endoalkylene containing 1 or 2 carbon atoms and the double bond of the tetrahydro compound being in 5,6-position, and the salts thereof as pharmaceutical preparations for oral administration and lowering of blood sugar level in the treatment of diabetes mellitus and the process for lowering the blood sugar level in the treatment of diabetes mellitus.

3 Claims, No Drawings

BENZENESULFONYL-SEMICARBAZIDES FOR LOWERING BLOOD SUGAR LEVELS

This is a division of application Ser. No. 149,746, filed June 3, 1971.

The present invention relates to benzenesulphonyl semicarbazides of the formula

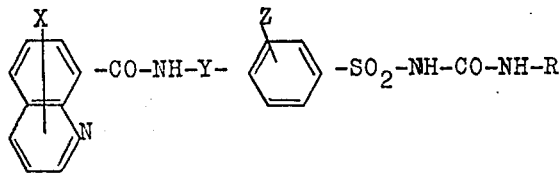

in which
X represents hydrogen, chlorine, bromine, methoxy or methyl,
Y represents $-CH(CH_3)-CH_2-$, preferably $-CH_2-CH_2-$,
Z represents hydrogen or a hydrocarbon radical having 1 or 2 carbon atoms which forms together with Y a 5- or 6-membered ring,
R represents
  a. an alkylene-imino radical having 3 to 7 carbon atoms in the ring, which may be unsaturated or substituted by 1 or 2 methyl groups or a lower alkyl group or a methoxy group,
  b. a pentamethylene-imino radical substituted by an endoalkylene group having 1 to 3 carbon atoms,
  c. a hexamethylene-imino radical substituted by an endoethylene group in $\beta$-$\epsilon$-position,
  d. a tetrahydro-isoindoline group, a 4,7-endoalkylenehexahydro-isoindoline group, a 4,7-endoalkylene-tetrahydro-isoindoline group, the endoalkylene group containing 1 or 2 carbon atoms and the double bond of the tetrahydro compound being in 5, 6 position.

The present invention moreover provides a process for the manufacture of these benzene-sulfonyl-semicarbazides, which comprises
  a. reacting benzenesulfonamides of the formula

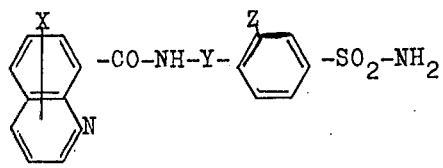

or salts thereof, with amino-carbamic acid esters, imino-thiocarbamic acid esters or imino-ureas containing as the imino group the group R—,
  b. reacting hydrazines of the formula $RNH_2$ or salts thereof with benzenesulfonyl-isocyanates, benzenesulfonylcarbamic acid esters, benzenesulfonyl-thiol-carbamic acid esters, benzenesulfonyl-carbamic acid halides or benzene-sulfonyl-ureas, substituted in 3-position by the group Z and in 4-position by the group

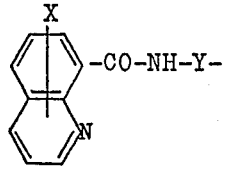

c. reacting benzenesulfo-chlorides of the formula

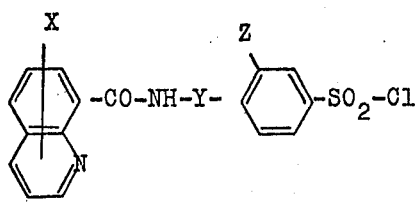

with R-substituted ureas,
  d. hydrolizing benzenesulfonyl-isourea ethers, benzenesulfonyl-isothiourea ethers or benzene-sulfonyl-imino-parabanic acid derivatives substituted by R, Z and

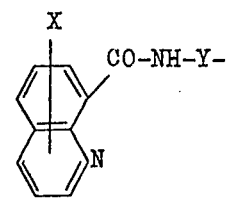

e. replacing in benzenesulfonyl-thioureas of the formula

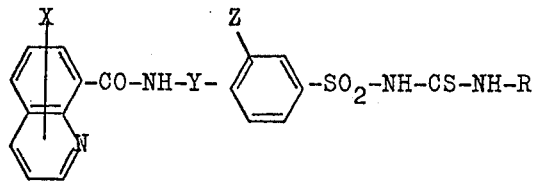

the sulfur atom by an oxygen atom, or
  f. introducing the radical

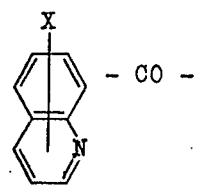

optionally step by step, into benzenesulfonyl-ureas of the formula

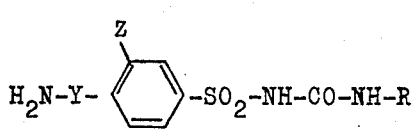

The benzene-sulfonyl-semicarbazides may then be treated, optionally for salt formation, with alkaline agents or physiologically tolerable inorganic or organic acids.

As semicarbazides or imino-ureas used for the syntheses mentioned sub (a), compounds of the formula R—NH—CO—NH$_2$ or acylated compounds of the formula R—NH—CO—NH-acyl are suitable, wherein acyl preferably stands for a low-molecular-weight aliphatic or aromatic acid radical, or diphenyl-semicarbazides of the formula R—NH—CO—N(C$_6$H$_5$)$_2$, wherein the phenyl radicals may be substituted or also linked to each other directly or by means of a bridge member, such as —CH$_2$—, —NH—, —O— or —S—, or N,N′-disubstituted carbohydrazides of the formula R—NH—CO—NH—R.

As benzenesulfonyl-carbamic acid halides the chlorides are preferably used.

Moreover, corresponding benzenesulfonyl-ureas which are unsubstituted at the nitrogen atom of the urea molecule not joined to the sulfonyl group or which are mono- or disubstituted by alkyl or aryl can be converted into the desired compounds by a reaction with hydrazines of the formula R—NH$_2$, optionally in salt form. Instead of benzenesulfonyl-ureas carrying such substituents, corresponding N-benzenesulfonyl-N′-acyl-ureas, benzenesulfonyl-carbamoyl-imidazoles, -pyrazoles or -triazoles or bis-(benzenesulfonyl)-ureas can also be used, which may carry at one of the nitrogen atoms a further substituent, for example methyl. For example such bis-(benzenesulfonyl)-ureas or N-benzenesulfonyl-N′-acylureas may be treated with hydrazines of the formula R–NH$_2$ and the salts thus obtained may be heated at an elevated temperature, advantageously at a temperature of at least 80°C.

The imino-carbamic acid esters or benzenesulfonyl-carbamic acid esters mentioned as well as the corresponding thio-esters advantageously contain in the ester component a low-molecularweight alkyl group or a phenyl group.

The benzenesulfonyl-isosemicarbazide ethers, benzenesulfonyl-isothio-semicarbazide ethers or benzenesulfonyl-parabanic acids also mentioned as starting substances can be obtained by reacting corresponding iso-semicarbazide ethers, isothio-semicarbazide ethers or parabanic acids with corresponding benzenesulfochlorides. Desulfurizing of the benzenesulfonyl-thiosemicarbazides in methanol first also yields benzenesulfonyl-thiosemicarbazide ethers which are then converted into benzenesulfonyl-semicarbazides by hydrolysis.

As regards the reaction conditions, the variations of carrying out the process of the invention may, in general, be modified within wide limits and can be adapted to each individual case. For example, the reactions may be carried out with the use of solvents, at room temperature or at an elevated temperature.

Depending on the nature of the starting substances, one or other of the aforesaid methods may, in some cases, provide a desired individual compound of the general formula only in a small yield or may be inappropriate for its synthesis. In such comparatively rare cases, the expert will have no difficulty in synthesizing the desired product according to one of the other methods of the process described.

The benzenesulfonyl-semicarbazide derivatives obtainable according to the invention are valuable medicaments which have a strong and long-lasting hypoglycemic action. The hypoglycemic action of the products of the invention can be ascertained by administering them to rabbits in a dose of 10 mg/kg of body weight and determining the blood sugar level according to the known method of Hagedorn-Jensen or by means of an auto-analizer for a prolonged period of time.

For example, it was found that, according to this method, 4-[4-(β-6-chloro-quinolino-8-carboxamido-ethyl)-benzenesulfonyl]-1,1-(3-methyl-pentamethylene)-semicarbazide - 3 hours after administration - brings about a lowering of the blood sugar level of 37%, after 24 hours 35% and after 48 hours still 30%.

The toxicity of the products of the invention is very low and is comparable to the very well tolerable N-(4-methylbenzenesulfonyl)-N′-n-butyl-urea.

The products of the invention are preferably used for the manufacture of pharmaceutical preparations suitable for oral administration and for the lowering of the blood sugar level in the treatment of diabetes mellitus, and may be used as such or in the form of their physiologically tolerable salts or in the presence of substances which cause such salt formation. For the formation of salts, there may be used, for example, alkaline agents such as alkali metal- or alkaline earth metal hydroxides and alkali metal or alkaline earth metal carbonates or bicarbonates or physiologically tolerable acids.

The present invention also provides a pharmaceutical preparation for oral administration and lowering the blood sugar level in the treatment of diabetes mellitus, which comprises a compound of the general formula (1) or a physiologically tolerable salt thereof in admixture or conjunction with a pharmaceutically suitable carrier.

The pharmaceutical preparations of the invention are preferably made up in the form of tablets and as pharmaceutically suitable carriers there may be mentioned, for example, talc, starch, lactose, tragacanth and magnesium stearate.

A pharmaceutical preparation, for example, a tablet or a powder, containing a benzenesulfonyl-semicarbazide of the invention or a physiologically tolerable salt thereof as the active substance, with or without one or more of the aforementioned carriers, is advantageously brought into a suitable dosage unit form. The dose chosen should comply with the activity of the benzenesulfonyl-semicarbazide used and with the desired effect. Advantageously, the dosage per unit amounts to about 0.5 to 100 mg, preferably 2 to 10 mg, but considerably higher or lower dosage units may also be used, which, when required, are divided or multiplied prior to their administration.

The following Examples illustrate the invention:

EXAMPLE 1

N-[4-(β-quinolino-8-carboxamido-ethyl)-benzenesulfonyl]-1,1-pentamethylene-semicarbazide 8.3 g of 4-(β-quinolino-8-carboxamido-ethyl)-benzenesulfonyl-methylurethane (m.p. 207° – 209°C, prepared from 4-(quinolino-8-carboxamido-ethyl)-benzene-sulfonamide and chloroformic acid methyl ester) were slightly boiled for 1 hour at a descending condenser in 100 ml of dioxan with 2 g of N-amino-piperidine. Subsequently, the dioxan was entirely evaporated under reduced pressure and the residue was recrystallized from dilute ethanol. The 4-[4-(β-quinolino-8-carboxamido-ethyl)-benzenesulfonyl]-1,1-pentamethylene-semicarbazide obtained melted at 149° – 152°C.

In an analogous manner there were obtained 4-[4-(β-quinolino-8-carboxamido-ethyl)-benzenesulfonyl]-1,1-(3-methylpentamethylene)-semicarbazide, m.p. 165° – 167°C (from dilute ethanol);

from 4-(β-6-chloro-quinolino-8-carboxamido-ethyl)-benzene-sulfonyl-n-ethyl-urethane (m.p. 199° – 201°C, prepared from 4-(β-6-chloro-quinolino-8-carboxamido-ethyl)-benzenesulfonamide and chloroformic acid methyl ester):

4-[4-(β-6-chloro-quinolino-8-carboxamido-ethyl)-benzenesulfonyl]-1,1-pentamethylene-semicarbazide, m.p. 174° – 176°C (from ethanol-dimethylformamide), 4-[4-(β-6-chloro-quinolino-8-carboxamido-ethyl)-benzenesulfonyl]-1,1-(3-methyl-pentamethylene)-semicarbazide, m.p. 195° – 197°C (from ethanol-dimethylformamide), 4-[4-(β-6-chloro-quinolino-8-carboxamido-ethyl)-benzenesulfonyl]-1,1-hexamethylene-semicarbazide, m.p. 188° – 190°C (from ethanol-dimethylformamide), 4-[4-(β-6-chloro-quinolino-8-carboxamido-ethyl)-benzenesulfonyl]-1,1-(3-ethyl-pentamethylene)-semicarbazide, m.p. 188°C (from ethanol-dimethylformamide);

from 4-(β-6-bromo-quinolino-8-carboxamido-ethyl)-benzenesulfonyl-methylurethane (m.p. 202° – 203°C, prepared from 4-(β-6-bromo-quinolino-8-carboxamido-ethyl)-benzene-sulfonamide and chloroformic acid methyl ester):

4-[4-(β-6-bromo-quinolino-8-carboxamido-ethyl)-benzenesulfonyl]-1,1-pentamethylene-semicarbazide, m.p. 196° – 197°C (from methanol-dioxan), 4-[4-(β-6-bromo-quinolino-8-carboxamido-ethyl)-benzenesulfonyl]-1,1-hexamethylene-semicarbazide, m.p. 188° – 190°C (from methanol - dioxan);

from 4-(β-5-methyl-quinolino-8-carboxamido-ethyl)-benzenesulfonyl-methylurethane (m.p. 184° – 185°C, prepared from 4-(β-5-methyl-quinolino-8-carboxamido-ethyl)-benzene-sulfonamide and chloroformic acid methyl ester):

4-[4-(β-5-methyl-quinolino-8-carboxamidoethyl)-benzenesulfonyl]-1,1-(3-methyl-pentamethylene)-semicarbazide, m.p. 170° – 171°C (from dilute methanol).

EXAMPLE 2

4-[4-(β-quinolino-8-carboxamido-ethyl)-benzenesulfonyl]-1,1-pentamethylene-semicarbazide 3.7 g of the sodium salt of 4-(β-quinolino-8-carboxamidoethyl)-benzene-sulfonamide were heated to 100°C for 3 hours with 3 g of 4,4-diphenyl-1,1-pentamethylene-semicarbazide in 20 ml of dimethylformamide. After cooling, water was added, the mixture was rendered alkaline by means of dilute ammonia and the diphenyl-amine was extracted by shaking it several times with ether. The aqueous phase was acidified with acetic acid after filtration. The precipitated 4-[4-(β-quinolino-8-carboxamido-ethyl)-benzenesulfonyl]-1,1-pentamethylene-semicarbazide was recrystallized from dilute ethanol and melted at 149° – 152°C.

EXAMPLE 3

4-[2-(6-chloro-quinolino-8-carboxamido)-indane-5-sulfonyl]-1,1-(4-methyl-pentamethylene)-semicarbazide 4.1 g of 2-(6-chloro-quinolino-8-carboxamido)-indane-5-sulfonamide (m.p. 250°C) were dissolved in 12 ml of dimethylformamide, the equimolar amount of sodium hydride was added and the whole was stirred for 10 minutes at room temperature. Then 2.0 g of pyrocarbonic acid ethyl ester were added and after another 10 to 15 minutes 1.7 g of N-amino-ζ-piperidine hydrochloride and 80 ml of absolute toluene were added. The mixture was heated for 2.5 hours to 120° – 130°C with slow distillation. The mixture was then allowed to cool and suction-filtered. The filtrate was concentrated and the residue was treated with dilute sodium hydroxide solution and methylene chloride. The alkaline solution was acidified with acetic acid and the precipitated substance was suction-filtered. The unreacted starting compound was separated by preparative thin-layer chromatography using silica gel PF 254. The sulfonyl-semicarbazide could be eluted with dimethylformamide. After vaporization of the solvent, the substance was dissolved in a solution of sodium carponate-bicarbonate, filtered through charcoal and precipitated by means of HCl. 4-[2-(6-chloro-quinolino-8-carboxamido)-indane-5-sulfonyl]-1,1-(4-methyl-pentamethylene)-semicarbazide, m.p. 219° – 220°C.

We claim:

1. A pharmaceutical preparation for oral administration and lowering the blood sugar level in the treatment of diabetes mellitus, which comprise a pharmaceutical carrier and about 0.5 to 100 mg. per unit dose of a benzenesulfonyl-semicarbazide of the formula

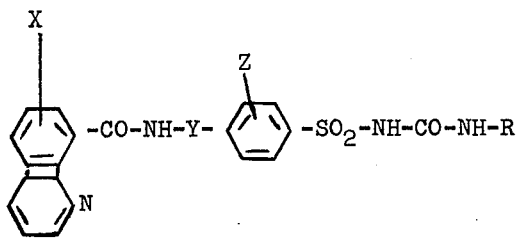

in which

X represents hydrogen, chlorine, bromine, methoxy or methyl,

Z is hydrogen or alkylene of 1 or 2 carbon atoms, which forms together with Y a 5-membered ring, Y represents —CH(CH$_3$)—CH$_2$—, or —CH$_2$—CH$_2$—, R represents a. alkylene-imino of 3 to 7 carbon atoms in the ring, which may be unsaturated or substituted by 1 or 2 methyl groups or lower alkyl group or methoxy group, a salt thereof of a pharmaceutically acceptable base or acid.

2. A pharmaceutical preparation for oral administration and lowering the blood sugar level in the treatment of diabetes mellitus according to claim 1 wherein the semicarbazide is 4-[4-(β-6-chloro-quinolino-8-carboxamido-ethyl)-benzenesulfonyl]-1,1-(3-methyl-pentamethylene)semicarbazide.

3. A process for lowering the blood sugar level in the treatment of diabetes mellitus, which comprises administering orally to the patient an effective amount in a unit dose from about 0.5 to 100 mg. of a benzenesulfonyl-semicarbazide as defined in claim 1 or a salt thereof of a pharmaceutically acceptable base or acid.

* * * * *

UNITED STATES PATENT AND TRADEMARK OFFICE
CERTIFICATE OF CORRECTION

PATENT NO. : 3,939,269
DATED : April 5, 1976
INVENTOR(S) : Aumuller et al.

It is certified that error appears in the above-identified patent and that said Letters Patent are hereby corrected as shown below:

In the Abstract and in the patent text at column 1, lines 15 and 50, column 2, line 25 and column 6, line 30 (claim 1), the quinolino group in the extreme left end of the structural formula should appear as:

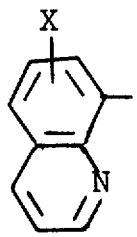

Signed and Sealed this

Twenty-fourth Day of August 1976

[SEAL]

Attest:

RUTH C. MASON
Attesting Officer

C. MARSHALL DANN
Commissioner of Patents and Trademarks